(12) United States Patent
Thundat et al.

(10) Patent No.: US 8,194,246 B2
(45) Date of Patent: Jun. 5, 2012

(54) PHOTOACOUSTIC MICROCANTILEVERS

(75) Inventors: Thomas G. Thundat, Knoxville, TN (US); Charles W. Van Neste, Kingston, TN (US); Gilbert M. Brown, Knoxville, TN (US); Lawrence R. Senesac, Knoxville, TN (US)

(73) Assignee: UT-Battellle, LLC, Oak Ridge, TN (US)

( * ) Notice: Subject to any disclaimer, the term of this patent is extended or adjusted under 35 U.S.C. 154(b) by 225 days.

(21) Appl. No.: 12/488,238

(22) Filed: Jun. 19, 2009

(65) Prior Publication Data

US 2010/0033723 A1 Feb. 11, 2010

Related U.S. Application Data

(63) Continuation-in-part of application No. 12/189,652, filed on Aug. 11, 2008, now Pat. No. 7,961,313, and a continuation-in-part of application No. 12/189,663, filed on Aug. 11, 2008, now Pat. No. 7,924,423.

(51) Int. Cl.
G01J 3/30 (2006.01)

(52) U.S. Cl. ............ 356/311; 73/643; 73/105; 356/432; 356/437

(58) Field of Classification Search .................. 356/402, 356/432, 337, 311; 73/643, 601
See application file for complete search history.

(56) References Cited

U.S. PATENT DOCUMENTS

| | | | |
|---|---|---|---|
| 4,255,971 A | 3/1981 | Rosencwaig | |
| 4,276,780 A | 7/1981 | Patel et al. | |
| 4,543,486 A | 9/1985 | Rose | |
| 4,678,905 A | 7/1987 | Phillips | |
| 4,897,541 A | 1/1990 | Phillips | |
| 4,931,384 A * | 6/1990 | Layton et al. | 435/7.31 |
| 5,036,708 A | 8/1991 | Urban et al. | |
| 5,118,608 A * | 6/1992 | Layton et al. | 435/7.1 |
| 5,141,331 A | 8/1992 | Oehler et al. | |
| 5,285,677 A | 2/1994 | Oehler | |
| 5,319,977 A | 6/1994 | Quate et al. | |
| 5,360,268 A | 11/1994 | Hayashi et al. | |

(Continued)

FOREIGN PATENT DOCUMENTS

DE 39 25 312 A1 4/1990

(Continued)

OTHER PUBLICATIONS

Van Neste, C.W., Senesac, L.R., and Thundat, T.; *Standoff photoacoustic spectroscopy*, Applied Physics Letters, 92; 2008; pp. 1-3.

(Continued)

*Primary Examiner* — Tarifur Chowdhury
*Assistant Examiner* — Isiaka Akanbi
(74) *Attorney, Agent, or Firm* — Brinks Hofer Gilson & Lione

(57) ABSTRACT

A system generates a photoacoustic spectrum in an open or closed environment with reduced noise. A source focuses a beam on a target substance disposed on a base. The base supports a cantilever that measures acoustic waves generated as light is absorbed by the target substance. By focusing a chopped/pulsed light beam on the target substance, a range of optical absorbance may be measured as the wavelength of light changes. An identifying spectrum of the target may detected by monitoring the vibration intensity variation of the cantilever as a function of illuminating wavelength or color.

26 Claims, 7 Drawing Sheets

U.S. PATENT DOCUMENTS

| | | | |
|---|---|---|---|
| 5,391,001 A | 2/1995 | Rupert et al. | |
| 5,440,388 A | 8/1995 | Erickson | |
| 5,977,538 A | 11/1999 | Unger et al. | |
| 6,006,593 A | 12/1999 | Yamanaka | |
| 6,379,210 B2* | 4/2002 | Xu et al. | 445/50 |
| 6,400,449 B2 | 6/2002 | Maris et al. | |
| 6,466,806 B1 | 10/2002 | Geva et al. | |
| 6,639,184 B1 | 10/2003 | Ennis | |
| 6,657,196 B2 | 12/2003 | Endo et al. | |
| 6,831,747 B2 | 12/2004 | Ferrell et al. | |
| 7,207,206 B2 | 4/2007 | Pinnaduwage et al. | |
| 7,243,548 B2* | 7/2007 | Thundat et al. | 73/590 |
| 7,245,380 B2 | 7/2007 | Kosterev | |
| 7,326,580 B2 | 2/2008 | Fukushima et al. | |
| 7,411,189 B2* | 8/2008 | Kawakatsu | 250/306 |
| 7,442,922 B2 | 10/2008 | Knebel et al. | |
| 7,448,269 B2 | 11/2008 | Shekhawat et al. | |
| 7,605,922 B2 | 10/2009 | Willing | |
| 7,665,364 B2* | 2/2010 | Su et al. | 73/643 |
| 7,679,063 B2* | 3/2010 | Hoffman et al. | 250/375 |
| 7,691,583 B2* | 4/2010 | Craighead et al. | 435/7.1 |
| 2004/0085540 A1 | 5/2004 | Lapotko et al. | |
| 2004/0120577 A1* | 6/2004 | Touzov | 382/190 |
| 2005/0070803 A1 | 3/2005 | Cullum et al. | |
| 2005/0117155 A1 | 6/2005 | Kosterev | |
| 2005/0201661 A1 | 9/2005 | Loock et al. | |
| 2005/0244747 A1 | 11/2005 | Nagai et al. | |
| 2007/0175760 A1 | 8/2007 | Thundat et al. | |
| 2007/0220978 A1 | 9/2007 | Su et al. | |
| 2007/0220979 A1 | 9/2007 | Su et al. | |
| 2008/0094614 A1 | 4/2008 | Tuschel et al. | |
| 2008/0276695 A1 | 11/2008 | Prater et al. | |
| 2009/0174884 A1 | 7/2009 | Kosterev et al. | |
| 2009/0321647 A1 | 12/2009 | Shelley et al. | |

FOREIGN PATENT DOCUMENTS

| | | |
|---|---|---|
| EP | 1 493 380 A1 | 1/2005 |
| JP | 11253794 A | 9/1999 |
| JP | 2001183294 A | 7/2001 |

OTHER PUBLICATIONS

Uotila, J and Kauppinen, Jyrki; *Fourier Transform Infrared Measurement of Solid-, Liquid-, and Gas-Phase Samples with a Single Photoacoustic Cell*; Applied Spectroscopy; vol. 62, No. 6; 2008; pp. 655-659.

Sievilia, P., Rytkonen, V-P, Hahtela, O, Chekurov, N., Kauppinen, J., Tittonen, I.; *Fabrication and characterization of an ultrasensitive acousto-optical cantilever*; Journal of Micromechanics and Microengineering; 17; 2007; pp. 852-859.

Lindley, R.E., Parkes, A.M., Keen, K.A., McNaghten, E.D., Orr-Ewing, A.J., *A sensitivity comparison of three photoacoustic cells containing a single microphone, a differential dual microphone or a cantilever pressure sensor*; Applied Physics B, Lasers and Optics; 86; 2007; pp. 707-713.

Koskinen, V., Fonsen, J., Kauppinen, J., Kauppinen, I., *Extremely sensitive trace gas analysis with modern photoacoustic spectroscopy*; Science Direct, Vibrational Spectroscopy; 42; 2006; pp. 239-242.

Ledermann, N., Muralt, P., Baborowski, J., Forster, M., Pellaux, J-P; *Piezoelectric Pb($Zr_x$, $Ti_{1-x}$)O3 thin film cantilever and bridge acoustic sensors for miniaturized photoacoustic gas detectors*; Journal of Micromechanics and Microengineering; 14; 2004; pp. 1650-1658.

Wells, P. N.T.; *A Vital Diagnostic Tool that Has Great Opportunities for Further Development*; IEEE Engineering in Medicine and Biology; Sep./Oct. 2000; pp. 14-20.

Crippa, P.R., Vecli, A., Viappiani, C.; *Time-resolved photoacoustic spectroscopy: new developments of an old idea*; New Trends in Photobiology (Invited Review); 24; 1994; pp. 3015.

PCT Seach Report and Written Opinion dated Feb. 6, 2010, PCT/US2009/052820, filed May 8, 2009.

C.W. Van Neste, L.R. Senesac, and T. Thundat, Standoff Detection of Explosive Residues Using Photothermal Microcantilevers, *Applied Physics Letters*, 92, 134102 (2008), © 2008 American Institute of Physics.

ORNL Demonstrates Suer-Sensitive Explosives Detector, Oakridger. com, Jun. 30, 2008.

Waghe, A., Kanan, S.M., Abu-Yousef, I., Jensen, B., and Tripp, C., Infrared Study of UV-Irradiated Tungsten Trioxide Powders Containing Adsorbed Dimethyl Methyl Phosphonate and Trimethyl phosphate, *Res. Chem Intermed*, vol. 32, No. 7, pp. 613-623, 2006.

Yang, P.W. and Casal, H.L., In Situ Diffuse Reflectance Infrared Spectroscopic Study of the Photodecomposition of Dibenzyl Ketone Adsorbed on Zeolites, *J. Phys. Chem*, 90, pp. 2422-2424, 1986.

PCT Seach Report and Written Opinion dated Dec. 14, 2009, PCT/US2009/052806, filed Aug. 5, 2009.

Uotila, J, *A new design of the differential photoacoustic gas detector combined with a cantilever microphone*, The European Physical Journal, Special Topics, vol. 153, Mar. 12, 2008, pp. 401-404.

Koskinen, V. et al., *Cantilever enhanced photoacoustic detection of carbon dioxide using a tunable diode laser source*, Applied Physics B, Lasers and Optics, vol. 86, No. 3, Jan. 23, 2007, pp. 451-454.

Kosterev, A. et al., *Applications of quartz tuning forks in spectroscopic gas sensing*, Review of Scientific Instruments, vol. 76, No. 4, Mar. 23, 2005, pp. 043105-1 043105-9.

Su, X. et al., *Quartz tuning fork biosensor*, Biosensors and Bioelectronics, Elsevier, vol. 17, No. 1/02, Jan. 1, 2001, pp. 111-117.

*XI International Scanning Probe Microscopy Conference 2009—Poster Session*; (8 pages).

Tetard et al., *New modes for subsurface atomic force microscopy through nanomechanical coupling*; Nature Nanotechnology (Letters) (Dec. 20, 2009); www.nature.com/naturenanotechnology.

*Crossing the line: how aggressive cells invade the brain*; R&D Mag Nov. 6, 2009; pp. 1-3; www.rdmag.com/.

Tetard et al., *Elastic phase response of silica nanoparticles buried in soft matter*; Applied Physics Letters 93; 133113 (Published on-line Oct. 2, 2008); pp. 133113-1-133113-3.

*First helium microscope is put through paces at NIST*; R&D Mag (Sep. 3, 2008); pp. 1-2; www.rdmag.com/News/2008/09/First-helium—microscope-is-put-through-paces-at-NIST.

*WITec Microscope Technology Win Prestigious 2008 R&D 100*; Chemie.De (Jul. 10, 2008); www.chemie.ded/news/e/84528.

*WITec Microscope Technology Wins Prestigious 2008 R&D 100 Award*; WITec; Jul. 2008 www.witec.de/en/company/witecnews/news.php?id=37.

Tetard et al., *Imaging nanoparticles in cells by nanomechanical holography*; Nature Nanotechnology Letters (Jun. 22, 2008); pp. 501-505; www.nature.com/naturenanotechnology.

Wouters, et al., *Automated Scanning Probe Microscopy for Combinatorial Polymer Research*; Mater.Res.Soc.Symp.Proc.vol. 894 (2006), pp. 111-117.

Shekhawat et al.; *Nanoscale Imaging of Buried Structures via Scanning Near-Field Ultrasound Holography*; Science Mag; vol. 310; Oct. 7, 2005; www.sciencemag.org; pp. 89-92.

Cuberes et al., *Heterodyne force microscopy of PMMA/rubber nanocomposites: nanomapping of viscoelastic response at ultrasonic frequencies*; J. Phys.D: Appl. Phys. 33 (2000); pp. 2347-2355.

Kolosov et al., *Nonlinear Detection of Ultrasonic Vibrations in an Atomic Force Microscope*; Jpn. J. Appl. Phys. vol. 32 (1993); pp. L 1095-L 1098.

Tetard et al., *New modes for subsurface atomic force microscopy through nanomechanical coupling*; Nature Nanotechnology (Supplementary Information); www.nature.com/naturenanotechnology; pp. 1-9, 20-28.

*AFM-Raman System*; Renishaw; pp. 1-3; http://www.renishaw.com/en/6638.aspx.

*MultiView 1000*; Nanonics Imaging Ltd.; pp. 1-7; http://www.nanonics.co.il/multiview-1000.html.

*MonoVista CRS*; Princeton Instruments; pp. 1-2; www.princetoninstruments.com/products/specsys/monovistacrs/.

*Alpha500 Automated Confocal Raman & Atomic Force Microscope*; WITec; www.witec.de.

*Alpha300A Atomic Force Microscope*; WITec; www.witec.de.

*Welcome to WITec*; WITec; www.witec-instruments.com/en/home/.

*Atomic Force Microscope alpha300 A*; WITec; www.witec-instruments.com/en/products/afm/alpha300a/.

*Confocal Raman and Atomic Force Microscope alpha 500*; WITec; www.witec-instruments.com/en/products/raman/alpha500/.
*Atomic force microscope*; Wikipedia, the free encyclopedia; pp. 1-7; http://en.wikipedia.org/wiki/Atomic_force_microscope.
*Lock-in Amplifier*; Wikipedia, the free encyclopedia; pp. 1-4 http://en.wikipedia.org/wiki/Lock-in_amplifier.

Google Search results for "mode synthesizing sensing atomic force microscopy", www.google.com/search?hl=en&ie=ISO-8859-1&q=mode+synthesizing+sensing+atomic+force+micro . . . ; (2 pages).

* cited by examiner

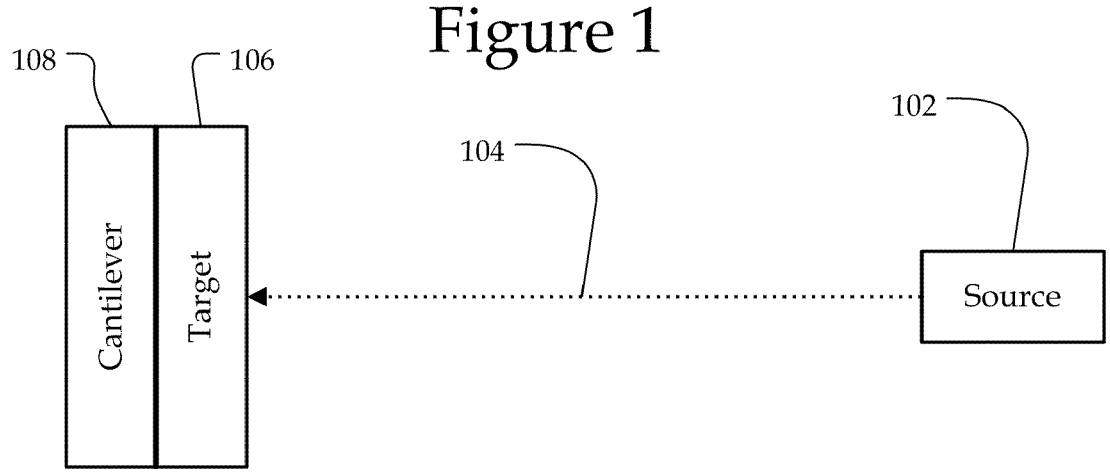
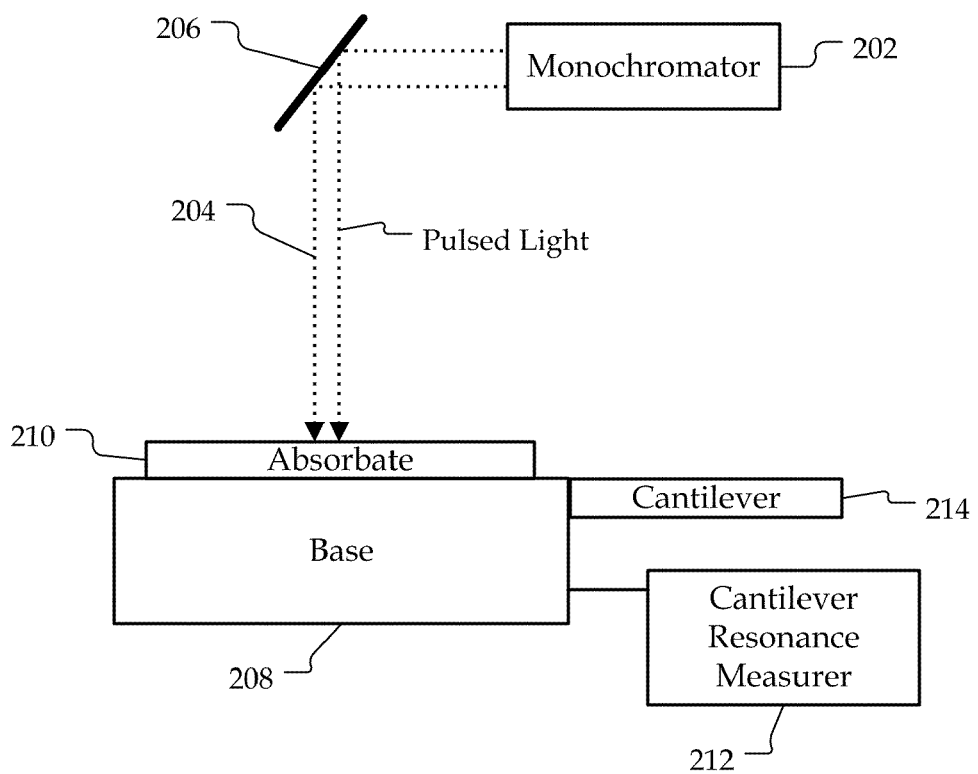

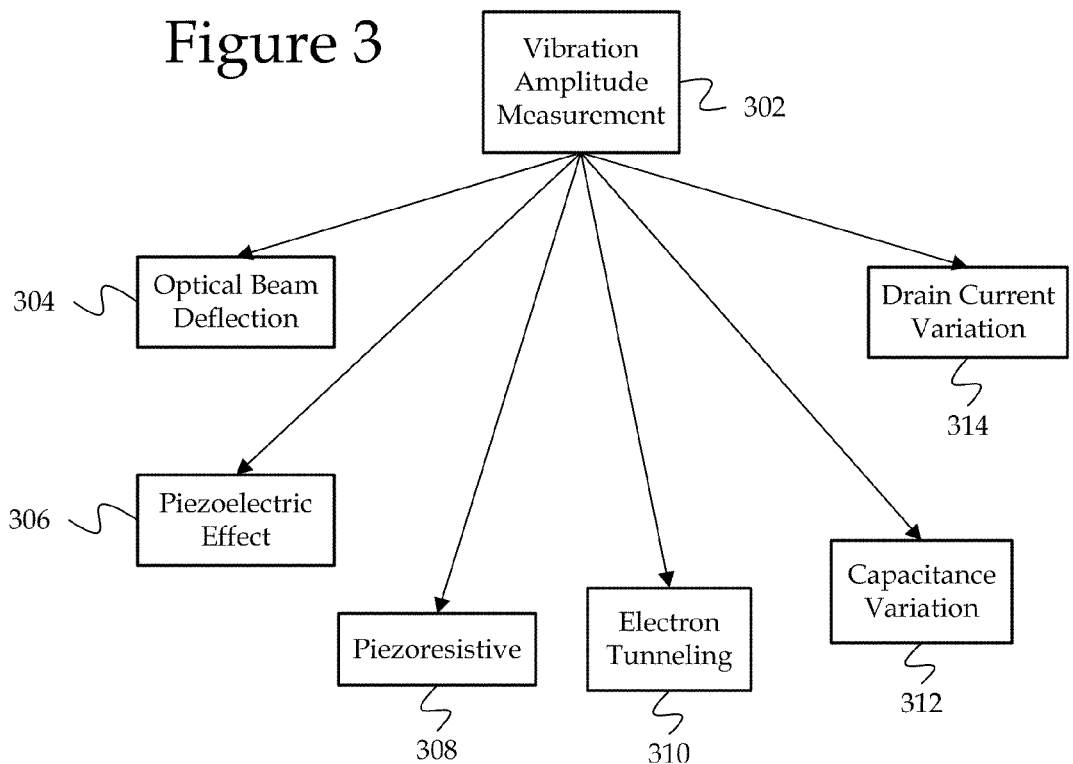
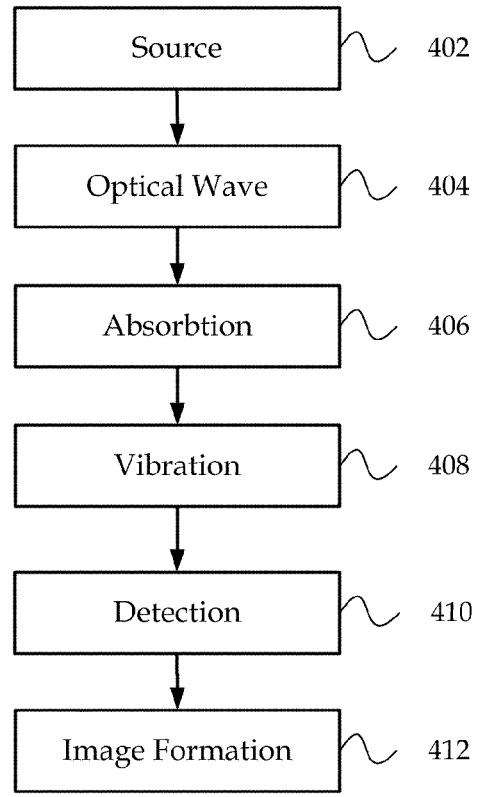

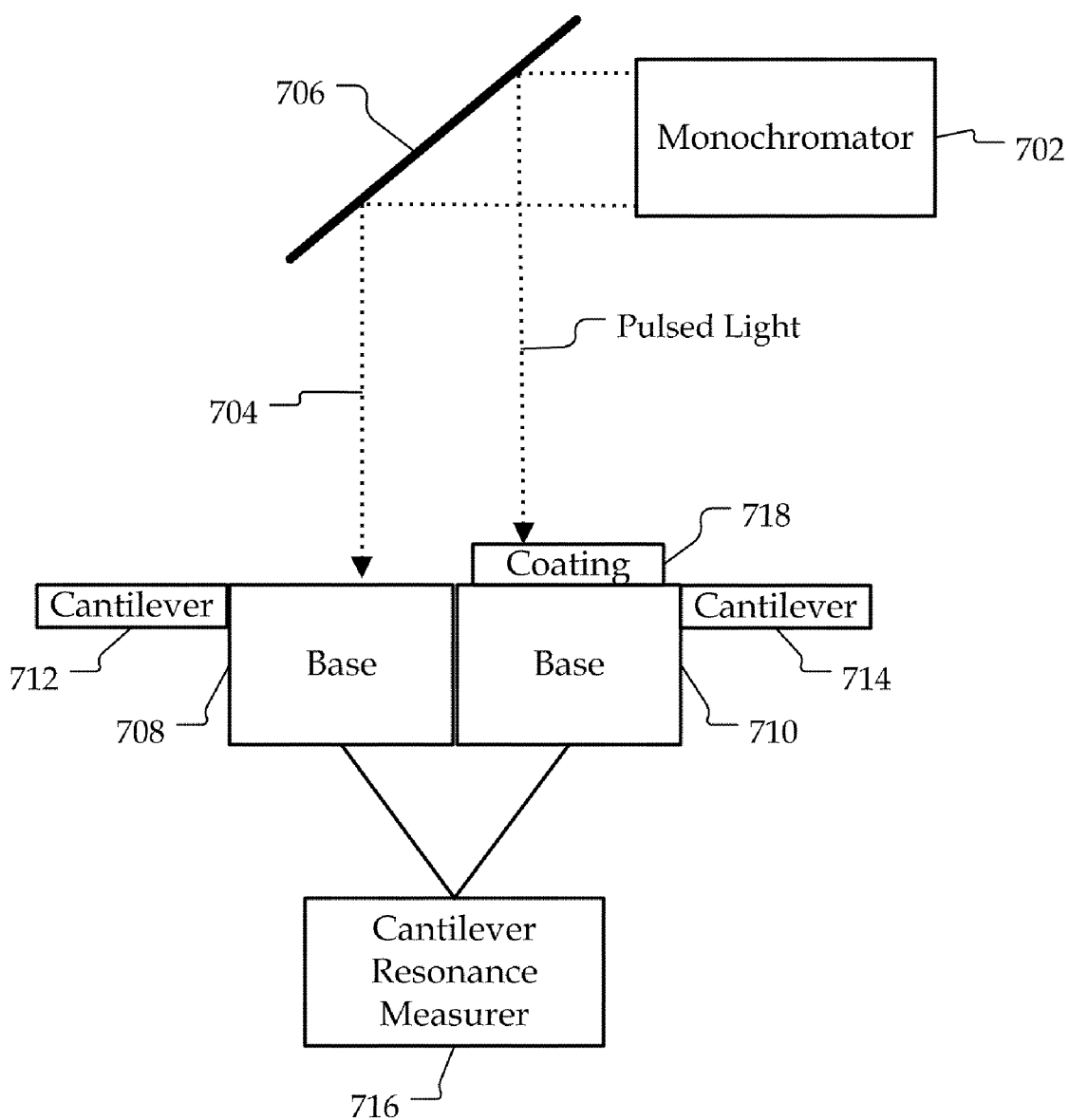

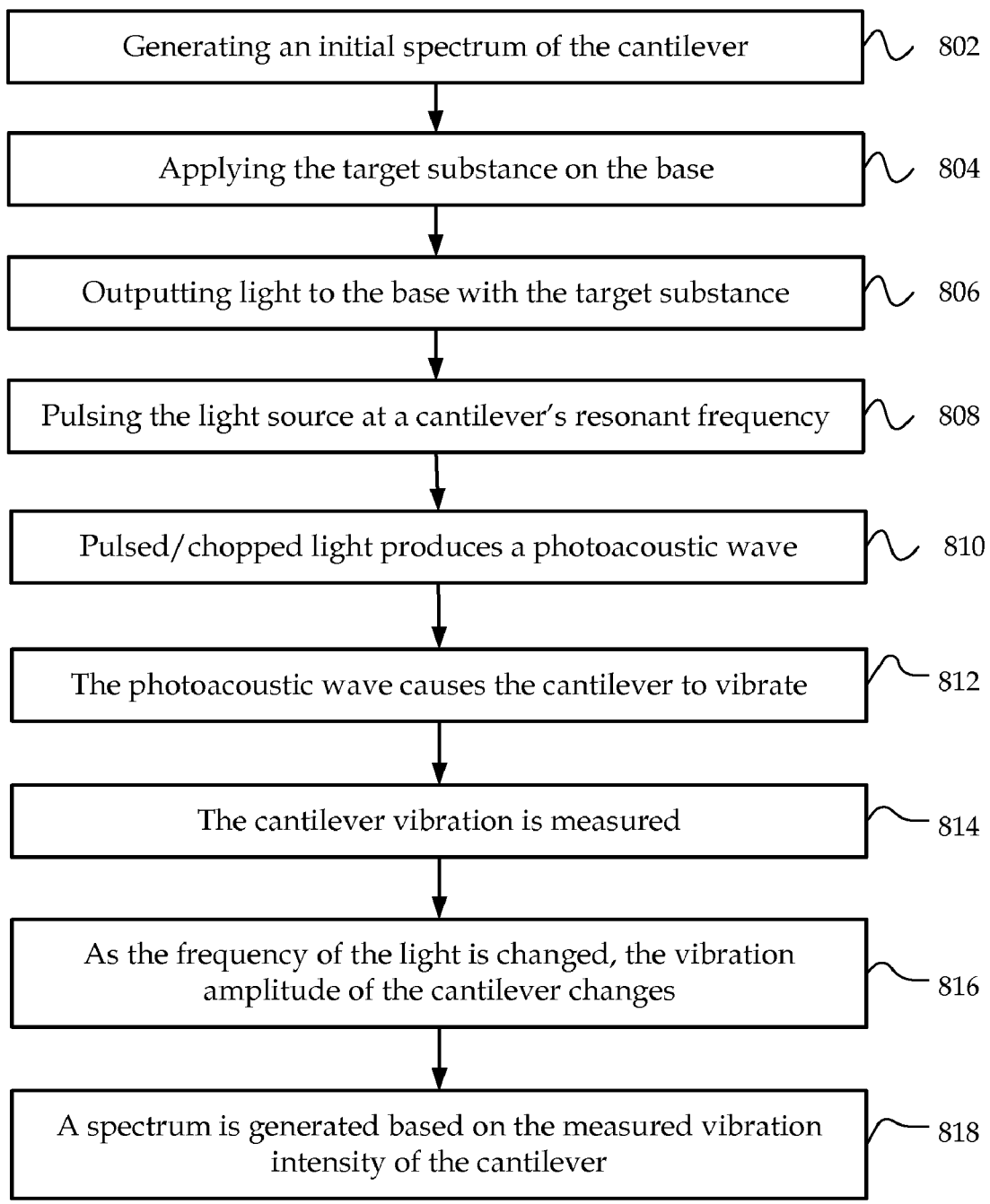

PHOTOACOUSTIC MICROCANTILEVERS

PRIORITY CLAIM

This application is a continuation-in-part to U.S. application Ser. No. 12/189,652, entitled "PHOTOACOUSTIC POINT SPECTROSCOPY," filed on Aug. 11, 2008, now U.S. Pat. No. 7,961,313. This application is also a continuation-in-part to U.S. application Ser. No. 12/189,663, entitled "REVERSE PHOTOACOUSTIC STANDOFF SPECTROSCOPY," filed on Aug. 11, 2008, now U.S. Pat. No. 7,924,423. Both of these applications are hereby incorporated by reference.

STATEMENT REGARDING FEDERALLY SPONSORED RESEARCH

This invention was made with government support under Contract No. DE-AC05-00OR22725 awarded by the U.S. Department of Energy. The government has certain rights in the invention.

BACKGROUND

Photoacoustic spectroscopy (PAS) may utilize the photoacoustic effect. The photoacoustic effect may include a conversion between light and acoustic waves due to absorption and localized thermal excitation. Light may be absorbed and transformed into kinetic energy. The absorption may result in local heating and a pressure/sound wave. The heat may vibrate the cantilever which is measured by chopping light on the cantilever. Alternatively, a measurement of the sound waves at different wavelengths may be used to generate a photoacoustic spectrum. In an open environment, it may be difficult to detect these waves. The waves may spread and stretch their energy outward and they may be exposed to environmental noise, which may reduce the range and sensitivity for producing a photoacoustic spectrum.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

FIG. 1 illustrates an exemplary photoacoustic point spectroscopy system;

FIG. 2A illustrates an exemplary spectroscopy system with a cantilever;

FIG. 3 illustrates exemplary measurement techniques;

FIG. 4 illustrates exemplary photoacoustic imaging;

FIG. 7 illustrates an alternative spectroscopy system with cantilevers; and

FIG. 8 is an exemplary process for photoacoustic point spectroscopy.

DETAILED DESCRIPTION

Figure 2B:
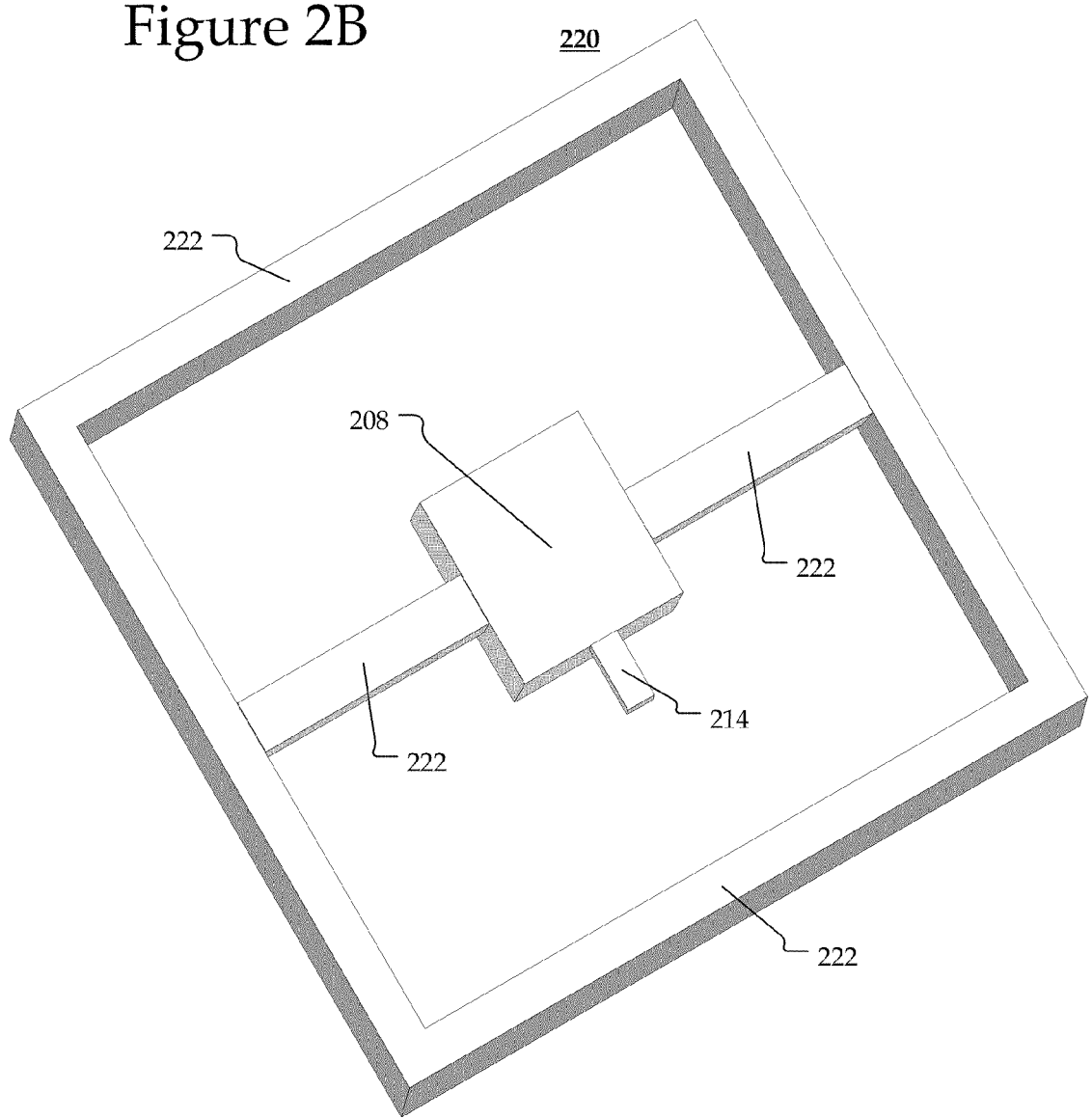
FIG. 2B illustrates an exemplary base arrangement.

A system generates a photoacoustic spectrum using a cantilever. A source may emit a beam to a target and a cantilever measures the generated signals. The target may be a material, residue, or molecule that is located adjacent to, disposed on, or coated on a base, such as a silicon substrate with an incident surface. The cantilever may be coupled to the base to measure the reaction resulting from the beam interacting with the target at the incident surface. By emitting a chopped/pulsed light beam to the target, it may be possible to determine the target's optical absorbance by monitoring the intensity of photoacoustic vibration produced by the light with the cantilever at different wavelengths. As the wavelength of light is changed, the target may absorb or reject each optical frequency. Rejection may decrease the photoacoustic intensity and absorption may increase the intensity, both of which in turn affect the vibration of the cantilever. Accordingly, an identifying spectrum of the target may be made with the photoacoustic wave intensity variation as a function of illuminating wavelength. The observed spectrum may correspond with the photoacoustic spectrum of the sample.

FIG. 1 is an exemplary photoacoustic spectroscopy system. Photoacoustic spectroscopy may measure the photoacoustic effect on a target substance or material with a cantilever. The spectroscopy system may include a source 102, a target 106, and a cantilever 108. The source 102 may include a static or tunable beamformer or a light source, such as a laser, monochromator, light emitting diode (LED), diode laser, LED pile, or the sun filtered through a grating.

The source 102 may provide an optical beam 104 to a target substance 106. The optical beam 104 may include a light beam, or a laser emission, such as a quantum cascade laser light source. The light source may be oscillatory, such that the optical beam 104 is chopped or pulsed at a predetermined, programmed, or adjustable frequency. The source 102 may be a laser that is tunable in its wavelength (color). The light source may be pulsed at a frequency that is equal to the cantilever mechanical resonance frequency discussed below. The pulsing frequency may be in the kilohertz range in one embodiment. The tunable wavelength (color) may be in the terahertz range in one embodiment. The optical beam 104 may include infrared, ultraviolet, or visible light, as well as x-ray radiation.

The target 106 may be a solid, liquid, or gas on or around the cantilever 108 or a base coupled to the cantilever 108 as shown in FIGS. 2A-2B. In one system, the target 106 may be a residue, such as an explosives or gun powder residue that is to be identified. In another system, the target 106 may be a residue from a surface at an airport that is tested for explosive and/or other material residues that are placed near the cantilever 108. Alternatively, the target 106 may be human tissue or cells, such that a medical doctor or researcher may test for skin cancer or other skin conditions by analyzing a spectrum of a cell. The spectra for cancer cells may be different from the spectra for normal cells.

The analysis of the spectrum of the target 106 may identify or determine various properties of the target substance 106. The optical beam 104 may be partially absorbed and/or partially rejected by the target 106 and that absorption or rejection is measured by the cantilever 108. When the target 106 absorbs the optical beam 104, an acoustic wave is generated that is measured by the cantilever 108. The generated acoustic wave may induce a vibration that is measured by the cantilever 108. The intensity of the acoustic wave may be proportional to the wavelength of the optical beam 104. The generated acoustic wave may produce the maximum vibration of the cantilever 108 when the pulse frequency of the optical beam 104 matches the resonant frequency of the cantilever 108.

The cantilever 108 may be a mechanical resonator that measures an acoustic signal. In addition, the cantilever 108 may vibrate based on the absorption of photon energy or absorption of other radiation when the cantilever 108 heats up from the absorbtion. The cantilever 108 may include a micro- or nano-cantilever beam that may measure the acoustic waves. The cantilever 108 may comprise a NEMS/MEMS device that may be any acoustic transducer fabricated to micrometer dimensions which may use other methods of sensing in addition to membranes and cantilevers. Likewise, the NEMS/MEMS device may be any acoustic transducer fabricated to nanometer dimensions which may use other methods of sensing in addition to membranes and cantilevers.

Acoustic waves may cause a vibration on the cantilever 108 as a result of the pulsed optical beam 104. Alternatively, absorbed energy from a light source may generate heat that vibrates the cantilever 108. The vibrations are processed to generate a photoacoustic spectrum. The intensity and frequency of the acoustic waves may depend on the wavelength and intensity of optical beam 104. The cantilever 108 may be coupled to an analysis apparatus, such as a computer system, for analyzing the target 106 through vibration of the cantilever 108.

FIG. 2A illustrates an exemplary spectroscopy system 200 with a cantilever. The spectroscopy system includes a monochromator 202 providing pulsed light 204 off a reflection plate 206 to an absorbate 210 on a base 208. The base is coupled to a cantilever 214 and a cantilever resonance measurer 212.

The monochromator 202 is an exemplary light source 102 that provides the pulsed light beam 204. The pulsed light beam 204 may be the pulsed optical beam 104, or a Fourier Transform Infrared Spectrometer (FTIR). Alternatively, a square wave pulse or sine wave pulse may be used for excitation. In one example, the pulsed light beam 204 is reflected off a reflection plate 206. The reflection plate 206 may redirect and focus the light towards a target 106, such as the absorbate 210.

The absorbate 210 is an exemplary target 106 that is illuminated by the pulsed light beam 204 in order to measure the photoacoustic effect from the absorption of the light by the absorbate 210. The absorbate 210 may also be referred to an analyte. The absorbate 210 may include biomaterials, such as biomass samples. The biomass sample may be placed on the substrate base 208 and exposed to different wavelengths of the pulsed light 204, so that the cantilever 214 motion may be monitored as a function of wavelength. In one example, the absorbate 210 molecules may absorb on the incident surface of the base 208 by diffusion, or a pump is used for collecting vapor samples from the air. It may also use a coating to preconcentrate a specific analyte on the substrate. The absorbate 210 may include tissues, cells, and other biomolecules and materials, as well as small quantities of powered materials. This technique may also be used under a solution, where a readout mechanism or display interfaced to the sensor that monitors the cantilever is selected to be compatible with liquid. As described, the absorbate 210 may absorb photon energy and the heat from the absorption vibrates the cantilever which is measured by chopping light.

The base 208 may be adjacent the absorbate 210, or the base 208 may be coated or covered with the target material or substance that comprises the absorbate 210. The base may be a substrate and/or be made of silicon. The incident surface of the base 208 may be illuminated with the pulsed light 204. The base 208 may include a relatively large surface or substrate. The surface thickness of the base 208 may include a thin membrane and the size of the thickness may vary. In one system, the surface may be one millimeter square or be several centimeters square.

FIG. 2B illustrates an exemplary base arrangement 220. In one embodiment, the base 208 with the cantilever 214 may be suspended by scaffolding 222. The scaffolding 222 may be separate pieces as shown, or may be a single component. The arrangement 220 may be micro-machined such that the base 208 is in a plane suspended from the scaffolding 222 of thicker silicon beams using thinner and weaker bridges. In one example, the arrangement 220 may be similar to the arrangement of micro hot plates.

The base 208 may be micro-machined with the cantilever 214 attached to one side of the base 208. In an exemplary system, the cantilever 214 is made from the same material as the base 208. The dimension of the cantilever 214 may also vary, such as a few microns to several hundred microns. The cantilever 214 may be about one micron in thickness, about 100 microns in length, and about 20 microns wide. These dimensions are merely exemplary, and the cantilever may be sized differently. In one system, the relatively larger surface area of the base 208 compared with the cantilever 214 may result in more analyte molecules of the absorbate 210 being absorbed on the substrate.

The cantilever 214 may be an exemplary vibratory sensor or detector. The cantilever 214 may be used to identify the molecules of the absorbate 210 by identifying a spectrum based on the absorbate 210. The cantilever 214 may be coupled to the base 208 that is coated with molecules of the absorbate 210. Vibratory detectors in addition to the cantilever 214 may include a standard, high-sensitivity microphone, NEMS or MEMS membrane, or a micro-/nano-cantilever beam. The cantilever 214 is excited by photoacoustic waves that are generated when the pulsed light 204 is absorbed by the target material or absorbate 210 at the surface of the base 208. Acoustic waves produced by the pulse/chop frequency of the pulsed light 204, mechanically oscillate the cantilever 214. The chop/pulse of the pulsed light 204 produces photoacoustic waves at the air/surface boundary of the base 208 which drive the cantilever 214 into mechanical oscillation. A photoacoustic spectrum is generated when the absorbed light is coupled to the molecules and used to mechanically excite the cantilever 214. The resonant frequency of the cantilever 214 may be dynamically monitored by the cantilever resonance measurer 212 and fed to the pulse/chop mechanism so that the pulsed light 204 is pulsated at the resonant frequency of the cantilever 214. The cantilever 214 may be placed in/around gasses, pressures, and/or temperatures that improve the maximum signal output of the device.

Figure 5:
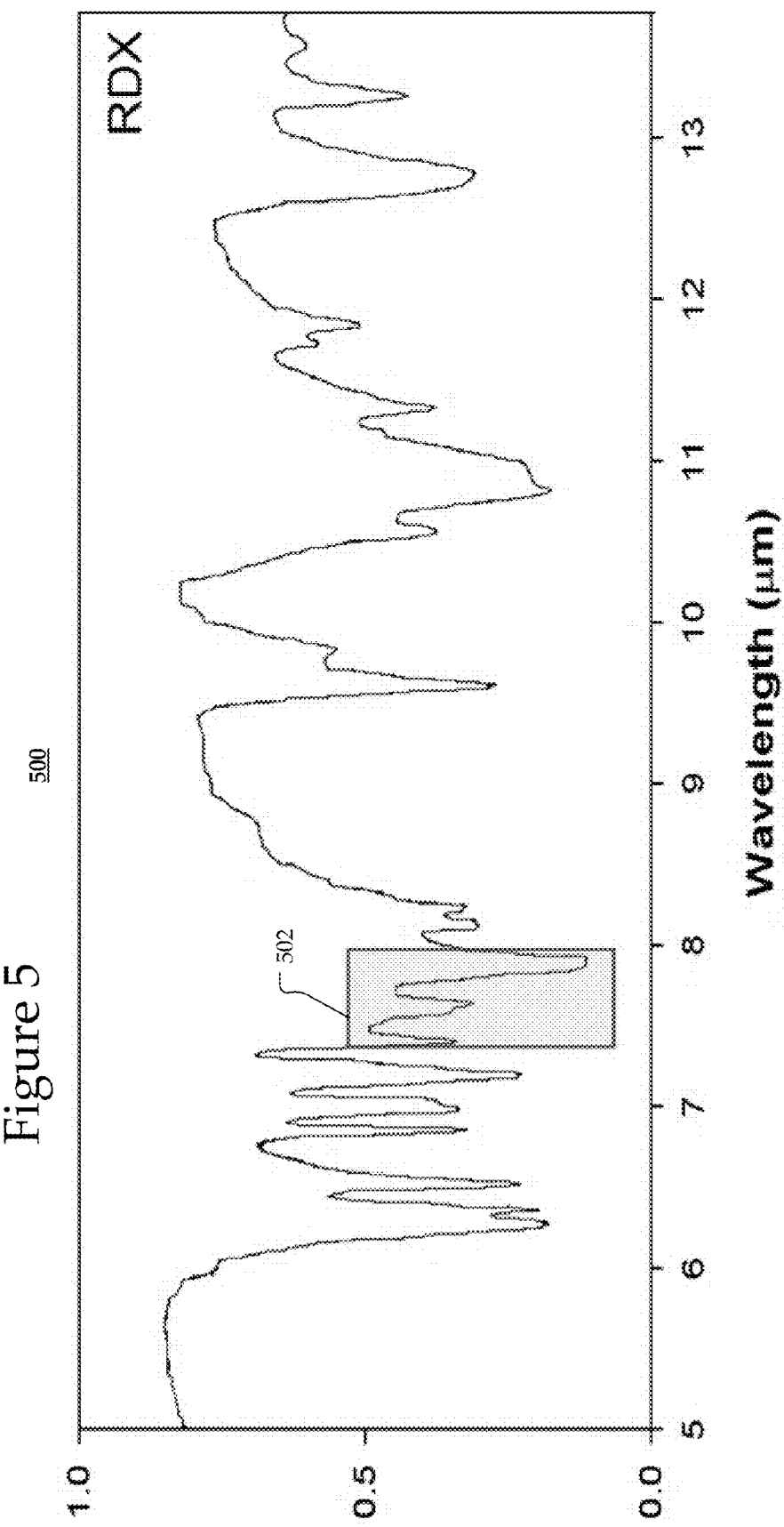
FIG. 5 is an exemplary spectrum of cyclotrimethylenetrinitramine (RDX)
Figure 6:
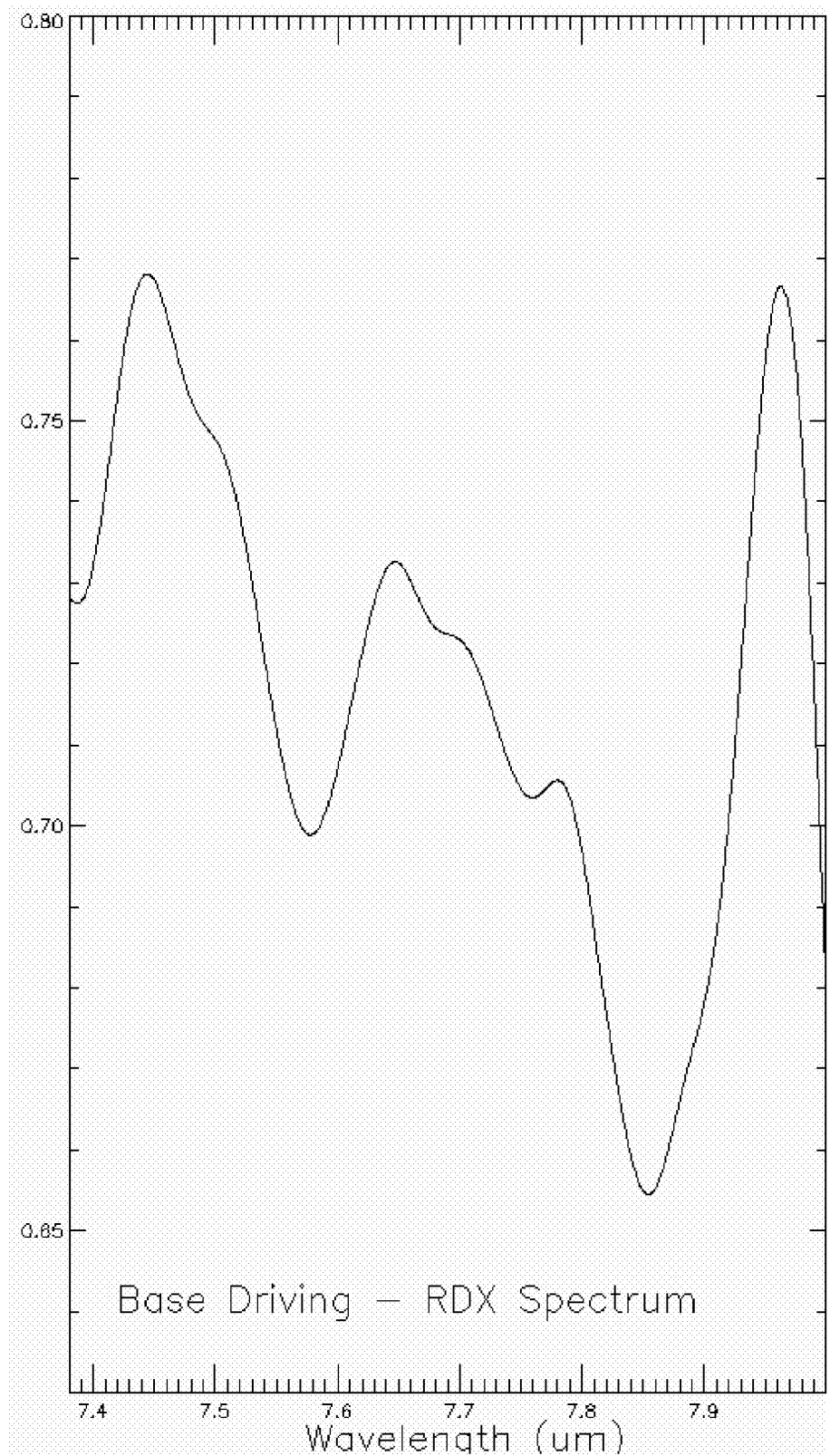
FIG. 6 is an exemplary photoacoustic spectrum.

When the wavelength (color) of the pulsed light 204 is changed, the molecules of the absorbate 210 may absorb or reflect more or less of the pulsed light 204. The corresponding photoacoustic waves generated by the molecular absorption of the pulsed light 204 may undergo increasing/decreasing amplitude as the optical wavelength is changed. This alters the vibrational amplitude of the cantilever's mechanical actuator (tine, diaphragm, etc.). When the absorbate 210 molecules absorb specific wavelengths of the pulsed light 204, the acoustic wave intensity changes, which changes the vibration amplitude of the cantilever 214. An identifying spectrum of the cantilever 214 and the attached absorbate 210 may be generated based on the vibrational amplitude of the cantilever 214 versus the optical wavelength of the pulsed light 204. The identifying spectrum may be derived after subtracting out an initial spectrum taken of the cantilever 214 without the absorbate 210, such as in the embodiment described with respect to FIG. 7. FIGS. 5-6 illustrate exemplary spectra.

FIG. 3 includes exemplary vibration amplitude measurement 302 techniques that may measure the vibration amplitude of the cantilever 214. The cantilever resonance measurer 212 may measure the vibration of the cantilever 214 using the vibration amplitude measurement 302 techniques. There may be additional measurement types that are used for monitoring and measuring vibration. Optical beam deflection 304 includes a diode laser beam that is reflected off the free end of the cantilever into a position sensitive detector. The piezoelectric effect 306 may include coating the cantilever with a piezoelectric material, such that the vibration of the cantilever 214 may create a voltage due to piezoelectric effect. The cantilever vibration may also be measured by the piezoresistive 308 method where a doped channel in the cantilever 214 may change its resistance due to cantilever motion.

Other methods for measuring cantilever response includes electron tunneling 310, capacitance variation 312, and variation in the drain current 314 of a field effect transistor (FET) imbedded near a base of the cantilever 214. In electron tunneling 310, an electrically conducting cantilever is fabricated with a sharp tip as in the case of atomic force microscopy and placed in close contact with a conducting surface. When electrically biased, electrons tunnel from the cantilever tip to the conducting surface when the gap distance between the cantilever tip and the substrate is approximately a few nanometers. The tunnel current, which may be in the range of pico to nano amperes depending on the separation distance, may be measured using high sensitivity electronic circuits such as those used in scanning tunneling microscopy. It may also be possible to have a feed back circuit and a piezoelectric mount on the conducting substrate to keep the tunnel junction constant. In the capacitance variation technique 312, the cantilever and a substrate separated by a couple microns may be used similar to a parallel plate capacitor. The capacitance between the cantilever and the substrate changes as a function of distance between them. In the FET-based cantilever deflection measurement 314, a FET is imbedded at the fixed end of the cantilever with stress from cantilever bending directly affecting the base of the FET. Any bending of the cantilever may result in changes in carrier mobility and changes in the drain current.

FIG. 4 illustrates exemplary photoacoustic imaging. A source 402 provides an optical wave 404, such as a light beam, to a target. The source 402 may be a monochromator, such as the monochromator 202 illustrated in FIG. 2A. The optical wave 404 is pulsed or chopped before being partially or fully absorbed 406 by the target. The target may be an absorbate or analyte that is disposed on or near a surface of a base. The base may include or be coupled to a cantilever. The pulsing of the optical wave generates an acoustic wave that generates a vibration 408 on the cantilever. Certain frequencies of the optical wave 404 will be absorbed, while other frequencies may be rejected by the target. As the light is absorbed or rejected, the acoustic wave's amplitude varies, which varies the vibration 408 of the cantilever. The cantilever vibration 408 may be measured or detected 410. The cantilever's output may form an image 412 that may be rendered by a display. The detection 410 may include an amplification of the measured waves. For example, the image formation 412 may be a photoacoustic spectrum of the target that is used to identify that target. As the color of the optical wave 404 is changed, the target will absorb 406 certain wavelengths (e.g. colors) better than others. This may vary the intensity of the optical waves 404 illuminated on the detector, which in turn may vary the acoustic waves generated at the detection 410 and change the resonant vibration detected by the cantilever.

FIG. 5 is a mid-infrared spectrum 500 of cyclotrimethylenetrinitramine (RDX). The spectrum 500 of RDX may be compared with the spectrum 600 discussed below that was taken using the using the system/methods described herein. RDX is a chemical used in various explosive devices. The mid-infrared spectrum 500 includes a portion 502 that is a color region in the mid-infrared range that may be compared with the spectrum shown in FIG. 6. The mid-infrared spectrum 500 may be a well accepted IR spectrum for RDX. The y-axis of mid-infrared spectrum 500 shows the percentage of light that is absorbed by the RDX. The x-axis represents the different colors of IR light (this quantity measured in optical wavelengths) scanned over the RDX. Together, the graph shows the percentages of light absorbed at each infrared color. This spectrum is unique to only RDX and no other chemical molecule will produce the same spectrum. In this way, RDX may be identified when a spectrum is taken matching mid-infrared spectrum 500. The techniques and the system described may be used on a variety of chemicals, elements, or other substances, and RDX is merely used as an exemplary spectrum. The spectra for other substances are different.

FIG. 6 is an exemplary photoacoustic spectrum 600 taken using the methods and/or systems described herein. The optical source used for generating the spectrum 600 may be a quantum cascade laser. The spectrum 600 of FIG. 6 includes a subset of the range from the spectrum 500 of FIG. 5. The color range of the quantum cascade laser used for generating the spectrum 600 of FIG. 6 is shown in portion 502 of FIG. 5. As illustrated, the spectrum 600 displays the same three absorption peaks shown in portion 502 of FIG. 5. The use of additional quantum cascade lasers or a light source with a greater color range may be used to extend the range of the spectrum 600.

FIG. 7 illustrates an alternative exemplary spectroscopy system 700 with multiple cantilevers. The system 700 may be similar to the system 200 illustrated in FIG. 2A, except it includes an array or plurality of cantilevers that may vibrate based on the reception of the same source of light or may individually receive light from independent sources. As shown in FIG. 7, there is a single light source, such as a monochromator 702 that provides pulsed light 704 that is reflected off a reflector 706. The pulsed light 704 is directed toward two bases 708, 710. The bases 708, 710 are attached to cantilevers 712, 714, respectively. In alternative systems, there may be a single base with multiple cantilevers. In some systems, each base is coupled to a corresponding cantilever as shown. A cantilever resonance measurer 716 may measure the detected vibrations from the cantilevers 712, 714. Alternatively, there may be a separate cantilever resonance measurer for each cantilever 712, 714. System 700 illustrates two substrate bases 708, 710, with one base 710 including a coating 718, where the other base 708 does not include a coating. The coating 718 may be a target substance. Accordingly, the base 708 and coupled cantilever 712 may be used as a reference for comparison with the base 710 and coupled cantilever 714 which include the coating 718. The vibration difference between the cantilevers 712, 714 may be measured and attributed to the coating 718. The common mode rejection between the coating covered substrate 710 and the reference substrate 708 may be used for eliminating interference.

In some applications, the system 700 may include more than two bases and attached cantilevers. An array of sources may emit optical waves on an area of bases and corresponding cantilevers. Alternatively, a single light source may be split or directed onto each base of an array of bases. Each base with a cantilever may be independent and measure vibration on its respective cantilever from the light source. Each substrate may be immobilized with partially selective, reversible coatings for preconcentration.

FIG. 8 is an exemplary process of measuring photoacoustic spectroscopy. In block 802, an initial spectrum of the cantilever is generated. The initial spectrum may measure vibration on the cantilever without a target substance. In block 804, the target substance is applied to the base that is coupled to the cantilever. In block 806, light is transmitted to the base that may support the target substance. One or more light sources provide one or more light beams focused on the base and the target substance that is disposed on a surface of the base. The light beams may be pulsed at approximately the cantilever's resonant frequency as in block 808. When an array of sources and an array of bases/cantilevers are used, each of the sources may be pulsed to correspond with the resonant frequency of a corresponding cantilever in a base/cantilever array.

Different types of target substances may react differently to the incoming light. In block 810, the pulsed light emitted on the target may result in generation of a photoacoustic wave. The photoacoustic wave created by absorption of the light from the target substance may cause the cantilever to vibrate as in block 812. In block 814, the vibration of the cantilever may be measured. The cantilever vibration may be a function of the color of the incoming light. In block 816, when the color of the light is changed, the vibration amplitude of the cantilever may change. The vibration changes are measured and a spectrum may be generated based on the measured vibration intensity of the cantilever as in block 818. The generated spectrum may be used to identify the target substance.

The system and process described above may be encoded in a signal bearing medium, a computer readable medium such as a memory, programmed within a device such as one or more integrated circuits, one or more processors or processed by a controller or a computer. For example, the cantilever resonance measurer 212, 716 may be a computer system that measures and records vibration data from cantilevers. That data may be analyzed in a computer system and used to generate and display spectra. If the methods are performed by software, the software may reside in a memory resident to or interfaced to a storage device, synchronizer, a communication interface, or non-volatile or volatile memory in communication with a transmitter. A circuit or electronic device designed to send data to another location. The memory may include an ordered listing of executable instructions for implementing logical functions. A logical function or any system element described may be implemented through optic circuitry, digital circuitry, through source code, through analog circuitry, through an analog source such as an analog electrical, audio, or video signal or a combination. The software may be embodied in any computer-readable or signal-bearing medium, for use by, or in connection with an instruction executable system, apparatus, or device. Such a system may include a computer-based system, a processor-containing system, or another system that may selectively fetch instructions from an instruction executable system, apparatus, or device that may also execute instructions.

A "computer-readable medium," "machine readable medium," "propagated-signal" medium, and/or "signal-bearing medium" may comprise any device that includes, stores, communicates, propagates, or transports software for use by or in connection with an instruction executable system, apparatus, or device. The machine-readable medium may selectively be, but not limited to, an electronic, magnetic, optical, electromagnetic, infrared, or semiconductor system, apparatus, device, or propagation medium. A non-exhaustive list of examples of a machine-readable medium would include: an electrical connection "electronic" having one or more wires, a portable magnetic or optical disk, a volatile memory such as a Random Access Memory "RAM", a Read-Only Memory "ROM", an Erasable Programmable Read-Only Memory (EPROM or Flash memory), or an optical fiber. A machine-readable medium may also include a tangible medium upon which software is printed, as the software may be electronically stored as an image or in another format (e.g., through an optical scan), then compiled, and/or interpreted or otherwise processed. The processed medium may then be stored in a computer and/or machine memory.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

We claim:

1. An apparatus for point spectroscopy comprising:
   a light source;
   an optical beam emitted from the light source that is chopped or pulsed at an optical frequency;
   a substrate that receives the optical beam from the light source on a surface of the substrate;
   a cantilever that is part of the substrate; and
   a target material that is disposed on the surface of the substrate, where the target material is subject to the optical beam and results in a photoacoustic induced vibration that is measured by the cantilever as the optical frequency is changed.

2. The apparatus of claim 1 where a photoacoustic wave is generated on the surface of the substrate from the target material absorbing at least a portion of the optical beam.

3. The apparatus of claim 2 where the vibration that is measured by the cantilever is induced by the generated photoacoustic wave.

4. The apparatus of claim 3 further comprising a cantilever resonance measurer that measures the vibration detected by the cantilever.

5. The apparatus of claim 4 where the vibration is detected by optical beam deflection, a piezoelectric effect, a piezoresistive effect, electron tunneling, capacitance variation, drain current variation, or a combination.

6. The apparatus of claim 4 where the cantilever resonance measurer comprises a processor that analyzes the cantilever vibration as the optical frequency is changed to generate a spectrum.

7. The apparatus of claim 1 where the optical pulse frequency corresponds with a resonant frequency of the cantilever.

8. The apparatus of claim 7 where the cantilever comprises a mechanical resonator, where the optical pulse frequency corresponds with a resonant frequency of the mechanical resonator.

9. The apparatus of claim 1 where the target material is coated or covered over the surface of the base.

10. The apparatus of claim 1 where the target material comprises analyte molecules that are absorbed on the surface of the base.

11. The apparatus of claim 1 where the cantilever is micromachined from the substrate.

12. The apparatus of claim 11 where the substrate and cantilever comprise a silicon substrate.

13. The apparatus of claim 1 where the substrate is a micromachined monolithic structure suspended from scaffolding using thin flexible bridges.

14. A system for array spectroscopy comprising:
   at least one source that emits at least one pulsed light beam at a programmed frequency;
   an array of base substrates that each comprise an incident surface;
   an array of cantilevers that correspond with the array of base substrates, where each base substrate is coupled to one of the cantilevers, further where each of the cantilevers includes a predetermined resonant frequency that corresponds with the predetermined chop frequency from at least one of the sources; and
   a target material that is disposed on one or more of the base substrates such that the incident surface of the one or more base substrates includes the target material and the pulsed light beams are directed at the target material;
   where the target material reacts with the pulsed light beam to generate a photoacoustic wave that produces a vibration of the corresponding cantilever that is measured as the optical color is varied, further where one of the base substrates does not include the target material on its incident surface and that base substrate is used as a reference.

15. The system of claim 14 where the base substrate without the target material is adjacent to at least one of the one or more base substrates that include the target material.

16. The system of claim 14 where the target material is coated on the incident surface of the one or more base substrates.

17. The system of claim 14 where each of the base substrates comprises a silicon substrate that includes the corresponding cantilever as a part of the silicon substrate.

18. The system of claim 14 where the measurement at each of the cantilever comprises an acoustic or vibrational measurement receiver that is tuned to the surface of the corresponding base substrate.

19. The system of claim 18 where a spectrum of the measurement correspond to the measured vibrational intensity at the optical colors of each of the sources.

20. The system of claim 19 where the vibration is detected by optical beam deflection, a piezoelectric effect, a piezoresistive effect, electron tunneling, capacitance variation, drain current variation, or combinations thereof.

21. The system of claim 14 where the at least one sources comprises a plurality of light sources or a single source with a grating that produces individual optical wavelengths corresponding to the base substrates in the base substrate array.

22. A method for photoacoustic spectroscopy comprising:
   chopping light emitted from a light source at a programmed frequency;
   focusing the emitted light towards an incident surface of a base substrate, where the base substrate includes a cantilever for monitoring a vibration from a target material that is disposed on the incident surface and that reacts to the emitted light;
   measuring the vibration of the cantilever by monitoring photoacoustic waves that are generated by the target material reacting to the emitted light; and
   measuring the vibration of the cantilever from photoacoustic waves that are generated from the reaction of the target material as the color of the emitted light is adjusted.

23. The method of claim 22 where the light source comprises a monochromator.

24. The method of claim 22 where the acoustic wave is generated on the incident surface of the base substrate because the target material absorbs at least a portion of the emitted light.

25. The method of claim 22 further comprising analyzing the measurements to generate a spectrum and identify the target material.

26. The method of claim 22 where the chopping frequency is substantially similar to a resonant frequency of the detector.

* * * * *